United States Patent
Shannon et al.

(10) Patent No.: US 6,319,279 B1
(45) Date of Patent: Nov. 20, 2001

(54) LAMINATED SELF-SEALING VASCULAR ACCESS GRAFT

(75) Inventors: Don Shannon, Mission Viejo; Chris Kuo, Orange; Benny Tu, Lake Forest, all of CA (US)

(73) Assignee: Edwards Lifesciences Corp., Irvine, GA (US)

( * ) Notice: Subject to any disclaimer, the term of this patent is extended or adjusted under 35 U.S.C. 154(b) by 0 days.

(21) Appl. No.: 09/419,315

(22) Filed: Oct. 15, 1999

(51) Int. Cl.[7] ............................................. A61F 2/06
(52) U.S. Cl. .............................. 623/1.44; 623/1.49
(58) Field of Search ................................. 623/1.39, 1.4, 623/1.1, 1, 1.44, 1.49

(56) References Cited

U.S. PATENT DOCUMENTS

| | | | |
|---|---|---|---|
| 5,061,276 | * 10/1991 | Tu et al. | 623/1 |
| 5,383,925 | * 1/1995 | Schmitt | 623/1 |
| 5,840,240 | 11/1998 | Stenoien et al. | 264/425 |
| 5,866,217 | * 2/1999 | Stenoien et al. | 623/1 |
| 5,897,587 | * 4/1999 | Martakos et al. | 623/1 |
| 5,931,865 | 8/1999 | Silverman et al. | 623/73 |

OTHER PUBLICATIONS

Perma–Seal Dialysis Access Graft Brochure, Possis Medical Inc., 9/99.

\* cited by examiner

*Primary Examiner*—Cary E. O'Connor
(74) *Attorney, Agent, or Firm*—Guy L. Cumberbatch; Peter Jon Gluck; Vascular Therapies

(57) ABSTRACT

A vascular access graft that is radially supported and self-sealing upon puncture with, for example, a dialysis needle. The graft has at least one access segment that is formed by an inner layer, an intermediate layer, and outer layer. The intermediate layer has, in longitudinal cross-section, regions of different densities. Radial support members within the intermediate layer prevent collapse of vascular access graft and may be formed of a material that has a lower melting temperature than the other components of the graft. A porous or low-density material is provided between the radial support members to permit blood seepage therein, and the graft is formed by heating to cause the radial support members to melt slightly into the interstitial spaces of the low-density material. The radial support members may be individual turns of a helical coil of FEP, and the low-density material may be compressed PTFE "cotton". The inner and outer layers may also be formed of PTFE. An adhesive layer of FEP may be provided closely surrounding the inner layer to further anchor the various components of the graft during the step of heating. The inner layer extends on either side of the access segment to provide junction segments that can be cleanly trimmed to size, and which can be used for graft cannulation in lieu of the access segment after suitable tissue ingrowth. A method of manufacture of the vascular access graft is also provided.

32 Claims, 4 Drawing Sheets

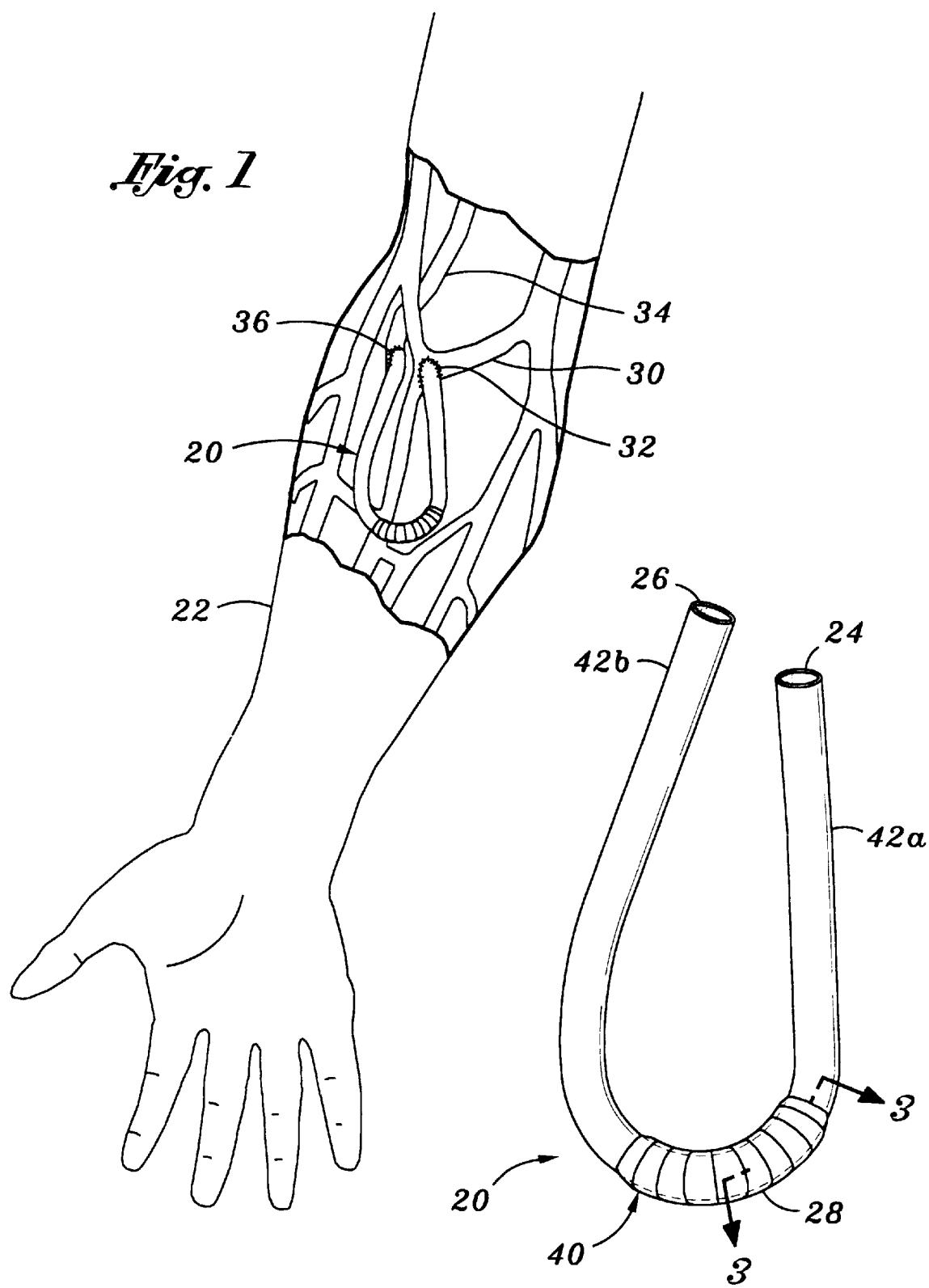

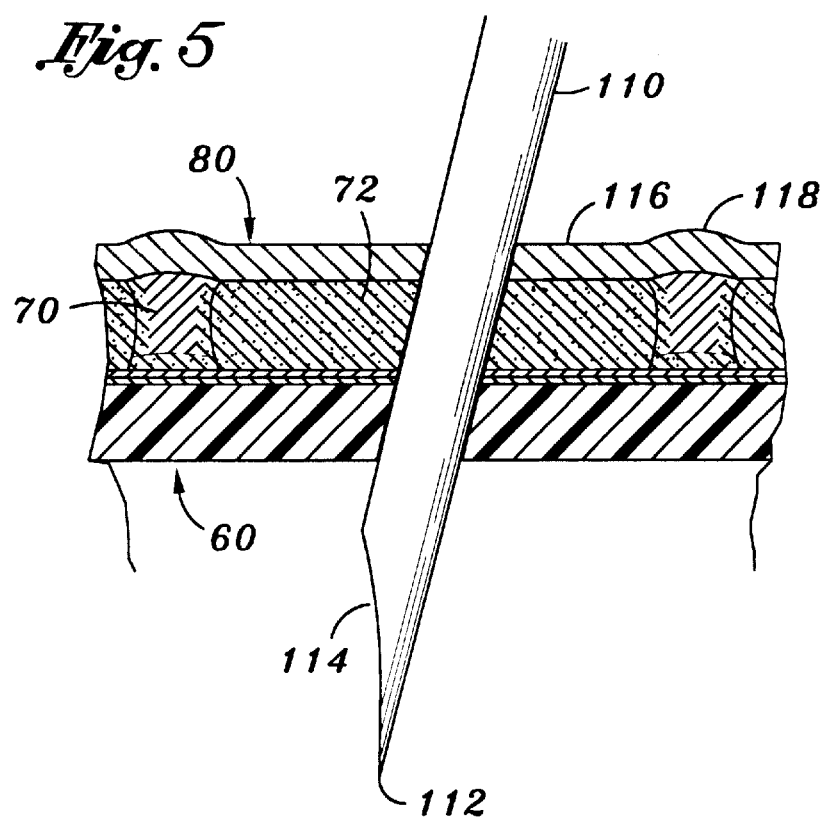
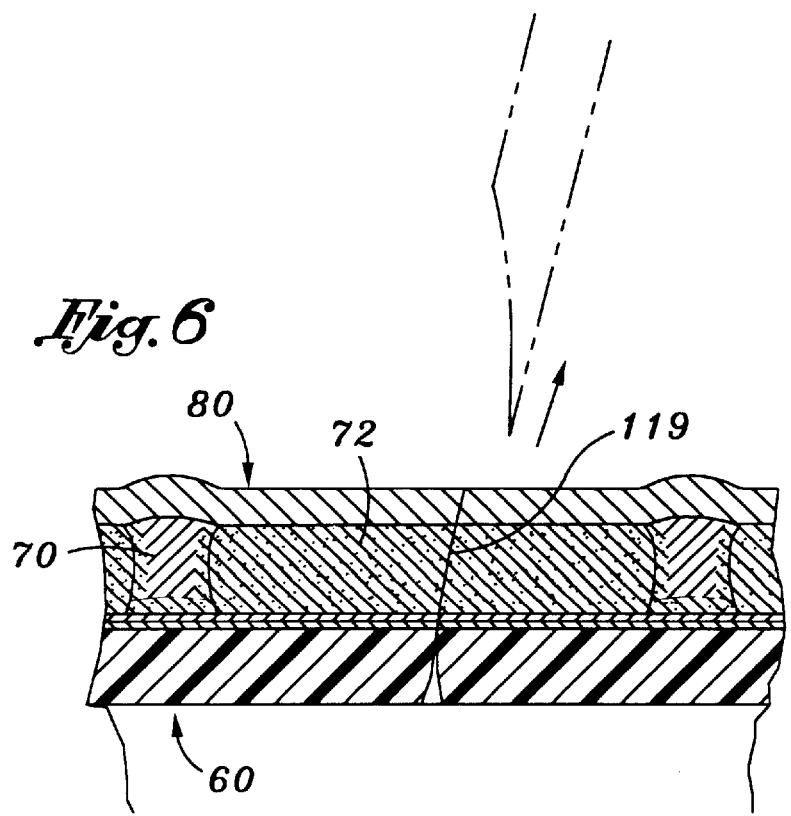

LAMINATED SELF-SEALING VASCULAR ACCESS GRAFT

FIELD OF THE INVENTION

The present invention relates to prosthetic vascular grafts and, more particularly, to a laminated vascular access graft that is self-sealing upon being punctured immediately after implant.

BACKGROUND OF THE INVENTION

Dialysis treatment of individuals suffering from renal failure requires that the blood be withdrawn and cycled through a dialysis machine that performs the function of the failed kidneys. This process, termed hemodialysis, must be repeated periodically and thus requires repeated puncture wounds using a dialysis needle. Moreover, dialysis requires a relatively rapid blood flow rate, typically above 200 ml/min, and so the dialysis needle is relatively large. Host vessels have insufficient strength to withstand collapse from such frequent puncturing with large bore needles.

A common technique to provide vascular access for hemodialysis, therefore, is to connect a prosthetic arteriovenous (AV) graft or shunt between an artery and a vein in, for example, the arm. The AV graft is constructed to withstand numerous puncture wounds or "sticks" without collapse.

Conventional AV grafts are typically constructed of woven or knitted polyethylene terepthalate (PET). Unfortunately, conventional AV grafts must be implanted for at least two weeks prior to puncture so that an intimal layer of fibrotic tissue has an opportunity to attach to the luminal surface of the graft. The layer of fibrotic tissue prevents blood leakage through the wall of the graft upon puncture. Prior to the time at which the graft can be safely punctured without leakage, a central venous catheter (CVC) must be utilized to collect the blood required for cycling through the dialysis machine. The CVC is needed because of the relatively high blood flow rates involved. For certain patients, however, use of a CVC is contraindicated.

Various attempts at designing a vascular access graft that will not leak if punctured immediately after implant have been made. One such graft is seen in the U.S. Pat. No. 4,619,641, in which the graft has two expanded polytetrafluoroethylene (PTFE) tubes in coaxial relationship with a space of about 1 mm therebetween filled with a self-sealing elastomer, such as silicone. Silicone often tends to stiffen the graft which is undesirable when trying to shunt between two fairly closely spaced vessels. In addition, silicone may have a tendency to exude inward through the puncture hole in the wall of the graft and therefore occlude the lumen.

Both U.S. Pat. Nos. 5,116,360 and 5,700,287 disclose vascular access grafts that ostensibly seal around puncture wounds. These two patents utilize various layers of fibers or other materials to slow the blood flow through the wall of the graft and cause its clotting.

Although the prior art includes many different designs of self-sealing vascular access grafts, none has proved effective in sealing around a puncture wound immediately after implant of the graft. Instead, grafts of the prior art exhibit excessive leakage or occlusion of the lumen. In some instances, occlusion of the graft lumen becomes so severe that the blockage within the graft must be removed in a process known as "revising" the graft. The procedure typically involves clamping the inflow end of the graft, making an incision to access the graft interior, clearing the block, and sewing the graft incision closed. Unfortunately, some self-sealing grafts are constructed in a manner that results in excessive fraying or layer dissection when they are incised, thus unduly lengthening or complicating the revision process.

Another drawback with some self-sealing grafts is their bulky construction that interferes with sensing of blood pressure pulsation. That is, as with a conventional needle stick of a natural vessel, the medical personnel establishing a dialysis circuit must "find" the graft under the skin. Searching for a pulse is one means of finding a vessel to be accessed, and thus excessive structure in some self-sealing grafts that attenuates the blood pressure pulses makes the search for the graft that much harder. Despite this drawback with thick-walled self-sealing grafts, the prior art has tended in the direction of more rather than less layers or barriers between the blood flow lumen and the graft exterior, under the theory that such layers or barriers enhance the goal of inducing a clot around a needle access site. Whether this theory works or not, the more layers or barriers the more attenuated is the blood pulse through the graft wall.

Because of the drawbacks associated with prior vascular access grafts, there is a need for an improved vascular access graft that enables rapid puncture immediately after implantation and resists collapse or lumen occlusion from repeated needle punctures.

SUMMARY OF THE INVENTION

The present invention comprises a vascular access graft that can be punctured and will seal about the puncture hole. The graft comprises an inner tube defining an inner lumen of the graft, and an outer tube concentrically disposed about the inner tube. An intermediate tubular layer is concentrically positioned between the inner and outer tubes, the intermediate tubular layer comprising, in longitudinal cross-section, alternating regions of materials of different densities, one of the materials being porous to blood. The material of the inner tube may be the same as the material of the outer tube, desirably PTFE. Further, the porous material of the intermediate layer may be the same material as both the inner and outer tubes. Desirably, the material of both the inner and outer tubes is PTFE that is substantially non-porous to blood, and the porous material of the intermediate layer is low-density PTFE.

In an exemplary embodiment, the intermediate tubular layer comprises a plurality of axially-spaced radial support members and regions of less dense material that is porous to blood axially interposed between the radial support members. The radial support members may comprise individual turns of a helical coil. The porous material of the intermediate layer is preferably low-density PTFE and the radial support members are made of a material that has a lower melting temperature that PTFE, such as, for example, FEP. In addition, the intermediate tubular layer may include a thin adhesive layer closely surrounding the inner tube and bonded to the regions of less dense material. Preferably, both the radial support members and the adhesive layer are formed of materials that have lower melting temperatures than the regions of less dense material, and the porous material of the intermediate layer comprises a low-density textile-like material that is longitudinally compressed from a relaxed state of the material.

In another aspect of the invention, a vascular access graft that can be punctured and will seal about the puncture hole is provided that comprises an inner tube defining an inner lumen of the graft, an intermediate tubular layer having a porosity and concentrically fitted around a portion of the inner tube, a plurality of radial support members concentrically fitted around the intermediate tubular layer, and an outer tube concentrically disposed about the intermediate tubular layer and radial support members. The plurality of radial support members may define axial spaces therebetween, with the intermediate tubular layer being further axially interposed between the radial support members. The intermediate tubular layer is desirably low-density PTFE and the radial support members are made of a material that has a lower melting temperature than PTFE, preferably FEP. A thin adhesive layer may closely surround the inner tube and be bonded to the intermediate tubular layer. In a particularly preferred embodiment, both the radial support members and the adhesive layer are formed of a material, e.g. FEP, that has a lower melting temperatures than the material of the intermediate tubular layer, which may be PTFE.

In another aspect, a method of manufacturing a vascular access graft is provided. The method comprises:

placing an inner layer on a mandrel, positioning a tube of low-density material over the inner layer, the tube having a first density, compressing the tube of low-density material to a second density higher than the first density, providing a plurality of axially spaced radial support members over the compressed tube of low-density material, closely surrounding the assembly of the tube of low-density material and radial support members with an outer tubular layer, and bonding the aforementioned components of the vascular access graft; and removing the mandrel.

Desirably, the step of bonding comprises heating, wherein the radial support members are made of the material that has a lower melting temperature than the melting temperature of low-density material, and the heating comprises heating the graft to a temperature between the respective melting temperatures of the radial support members and the low-density material. Preferably, the radial support members are made of FEP and the low-density material is made of PTFE. The method further may include longitudinally compressing the tube of low-density material to a second length shorter than the first length.

A further understanding of the nature advantages of the invention will become apparent by reference to the remaining portions of the specification and drawings.

BRIEF DESCRIPTION OF THE DRAWINGS

FIG. 1 is a cutaway perspective view of the arm of a patient showing a vascular access graft of the present invention attached as a shunt between an artery and a vein;

FIG. 2 is a perspective view of the vascular access graft of the present invention;

FIG. 5 is a detailed sectional view of the wall of the vascular access graft with a needle extending therethrough to withdraw fluids from within the inner lumen;

FIG. 6 is a detailed sectional view of the wall of the vascular access graft after the needle is withdrawn and showing the puncture wound sealed up.

DESCRIPTION OF THE PREFERRED EMBODIMENTS

Figure 3:
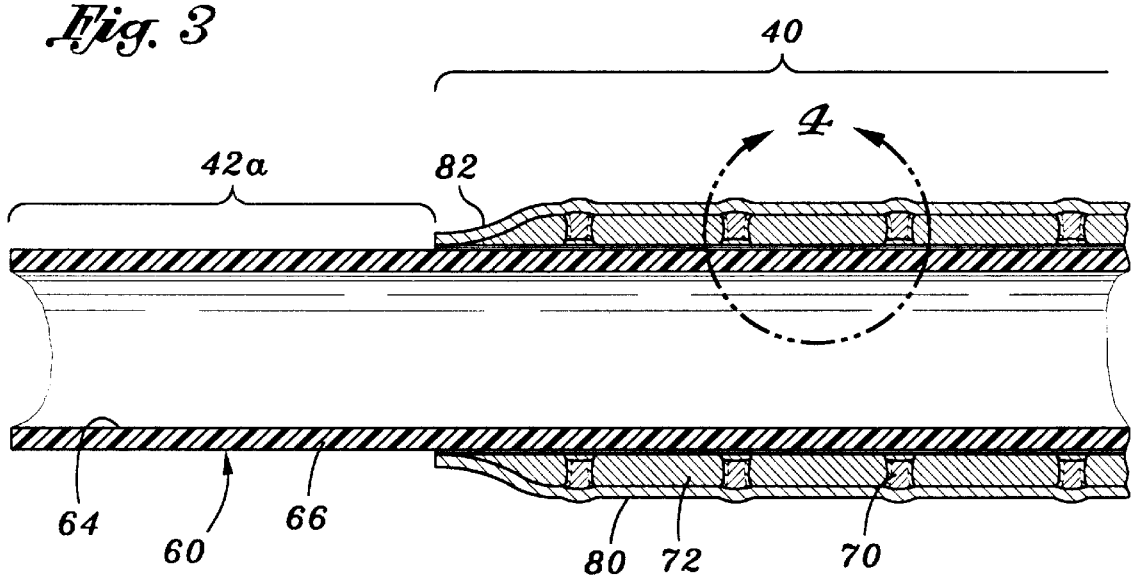
FIG. 3 is a cross-sectional view through the vascular access graft of FIG. 2 taken along line 3—3.

The present invention provides an improved vascular access graft with a portion that is self-sealing, enabling the graft to be punctured immediately after connection with the blood flow. At the same time, the early access portion of the graft is laminated to prevent the various tubular layers from dissecting, or separating, when stuck through with a needle, or when revised. Furthermore, the graft incorporates radial support members to prevent inward collapse upon repeated puncturing. The graft also includes segments on each end which can be cut to size and that are well-suited for forming anastomoses with blood vessels. Finally, the graft is highly flexible and constructed of durable and biocompatible materials for effective long-term implantation.

FIG. 1 illustrates a vascular access graft 20 of the present invention implanted in the vasculature of the arm 22 of a patient, with the subcutaneous layers around the area of implantation shown cut away. FIG. 2 illustrates the vascular access graft 20 isolated, showing an inflow end 24 and an outflow end 26 with a U-bend 28 therebetween. The inflow end 24 is seen in FIG. 1 connected to an artery 30 using a conventional anastomosis 32, while the outflow end 26 is connected to a vein 34 using another anastomosis 36. The particular anastomoses utilized may be varied, and are well-known in the art. The present graft 20 facilitates formation of secure anastomoses by virtue of its end structures, as will be explained below.

The vascular access graft 20 generally comprises a self-sealing early access segment 40 along the central portion, and a pair of junction segments 42a, 42b extending to the inflow and outflow ends 24, 26, respectively. The early access segment 40 may be repeatedly punctured with, for example, a dialysis needle or cannula to provide high flow access to the bloodstream. Importantly, the access segment 40 can be punctured immediately upon implantation, before any intimal layer tissue attachment. Although a single length of access segment 40 is shown, two or more discrete lengths may also be provided as desired. If more than one length of access segment 40 is provided, the region of the graft between the segments may be constructed identical to the junction segments 42a, 42b, or may incorporate other features that are not addressed herein.

As will be appreciated from FIG. 1, the vascular access graft 20 may need to be shortened from its initial length to fit within a particular patient's body cavity in proximity with the respective arteriovenous vessels. Either or both of the junction segments 42a, 42b can be reduced in the length to accommodate such custom fits. At the same time, the quality of the anastomoses 32, 36 is unaffected because the junction segments 42A, 42b are of conventional construction and can be trimmed to form relatively smooth oval or circular ends.

Figure 4:
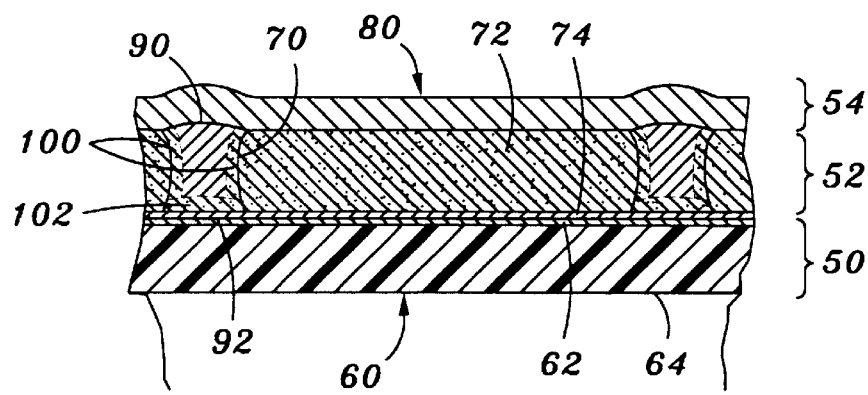
FIG. 4 is a detailed sectional view of one wall of the vascular access graft taken within the circle 4 of FIG. 3.

Now with reference to FIGS. 3 and 4, the detailed structure of the vascular access graft 20 will be described. FIG. 3 illustrates a portion of the graft 20 surrounding the interface between the early access segment 40 and the junction segment 42. The same construction applies to the interface between the access segment 40 and the other junction segment 42b. As seen in FIG. 4, the graft generally comprises an inner layer 50, an intermediate layer 52 concentrically surrounding the inner layer, and an outer layer 54 concentrically surrounding both the inner and intermediate layers. All three of these layers 50, 52, and 54, are present in the access segment 40, while only the inner layer 50 extends along the junction segments 42a and 42b.

The inner layer 50 comprises an inner or base tube 60 and an optional base tube reinforcement layer 62, seen best in FIG. 4. The inner wall of the base tube 60 defines a graft lumen 64, while the outer wall of the base tube (or of the reinforcement layer 62 if present) defines the outer surface 66 (FIG. 3) of the inner layer 50. In a preferred embodiment, the base tube 60 and reinforcement layer 62 are identical materials, with the former being an extruded tubular body and the latter being a thin tape helically wrapped therearound. The inner layer 50 is a material that is substantially non-porous to blood. More preferably, both the base tube 60 and reinforcement layer 62 are sintered, expanded PTFE, and the assembled base tube and reinforcement layer is available from Baxter International Inc., Vascular Systems Division of Laguna Hills, Calif., and sold under the product name LIFESPAN™. The inner layer 50 is available in diameters ranging from 4–28 mm, and has a superior burst strength of at least 150 psi due to the reinforcement layer 62.

As mentioned above, the junction segments 42a, 42b seen in FIG. 2 can be trimmed to size depending on the patient's need or surgeon preference. Because the inner layer 50 extends on either side of the access segment 40 to form the junction segments 42a, 42b, the quality of the graft mouth at the anastomosis is maximized. That is, the mouth is relatively smooth and there is minimal fraying. The length of the junction segments 42a, 42b depends on the overall length of the graft and the length of the access segment 40, which are given below.

The intermediate layer 52 comprises alternating regions of materials of different densities. More specifically, as seen in FIGS. 3 and 4, the intermediate layer 52 includes a plurality of axially spaced radial support members 70 with regions of porous or lower-density material 72 interposed therebetween. Additionally, the intermediate layer 52 preferably includes a thin adhesive layer 74 directly surrounding the inner layer 50.

The radial support members 70 may take a variety of forms, but are preferably made of a material that has a lower melting point than that of the low-density material 72. Further, the radial support members 70 also preferably have a lower melting point than the inner layer 50 and outer layer 54. One particularly preferred material is fluorinated ethylene propylene (FEP). In addition, the density of the radial support members 70 is greater than the low-density material 72, and is preferably sufficient to block the flow of blood therethrough. The radial support members 70 extend circumferentially around the graft 20 inbetween the inner layer 50 and the outer layer 54. In one embodiment, as will be described below, the radial support members 70 comprise a single helical coil, with individual turns of the coil being seen in the cross-sectional views of FIGS. 3 and 4. Alternatively, the radial support members 70 may be axially spaced circular rings that are closely fit about the inner layer 50, and may be held together with longitudinal connectors (not shown). Those of skill in the art will recognize that various other forms of the radial support members 70 are possible, so long as they radially support the early access segment 40 from collapse and have a lower melting point than that of the low-density material 72.

The porous or low-density material 72 may also take a variety of forms, as long as the melting temperature of the material used is higher than that of the radial support members 70. In this context, "porous" or "low-density" means a material that has interstitial spaces into which blood can flow. In a preferred embodiment, the low-density material 72 comprises a textile-like polymer sheet. Additionally, the low-density material 72 preferably has a first density in a relaxed or uncompressed state, but is incorporated in the graft 20 in a compressed state having a second, higher density. A particular preferred low-density material 72 is a PTFE "cotton" having a bulk or uncompressed density of between about 0.008–0.04 g/cc. The magnitude of compression and its effect on the density will be discussed below with respect to the graft assembly sequence seen in FIGS. 7A–7G.

The adhesive layer 74 comprises any suitable material that will adhere the radial support members 70 to the inner layer 50. Therefore, in a preferred embodiment, the adhesive layer 74 is a thin tape securely wound around the inner layer 50 and constructed of the same material as the radial support members 70 so that, upon melting, the support members 70 and adhesive layer 74 bond, or be laminated together. In an exemplary embodiment, the adhesive layer 74 is a tape of FEP having a thickness of about 0.01 mm (0.0004 inches).

Alternatively, the adhesive layer 74 is any suitable plastic with a similar melt temperature as the radial support members 70, and that will coalesce or otherwise bond to the support members upon the application of heat. One such suitable plastic is PVC. Conceivably, the adhesive layer 74 could have a higher melting temperature than the radial support members 70, but is made of a material or has properties that permit it to form strong bonds with the material of the support members upon contact therewith. For example, a thin metal tube or stent capable of forming bonds with the material of the support members 70 may even be used. The stent could be adhered to the inner layer 50 so that the support members 70, and thus the low-density material 72, are also fixed relative to the inner layer.

The outer layer 54 comprises an outer tube 80 that closely surrounds the intermediate layer 52. The outer tube 80 is made of a material that has a lower melting point than that of the low-density material 72, and is substantially non-porous to blood. As seen in FIG. 3, the outer tube 80 extends in a tubular fashion along the early access segment 40 and narrows radially inward at each end thereof, as indicated by the neck region 82. Desirably, the outer tube 80 is a material that forms an adhesive bond with the outer surface 66 of the inner layer 50. In this regard, the neck region 82 contacts and seals with the outer surface 66. In a preferred embodiment, the outer surface 66 comprises the reinforcement layer 62, and the outer tube 80 is formed of the same material, preferably PTFE.

With reference to the detailed sectional view of FIG. 4, various melt regions within the intermediate layer 52 can be seen. As mentioned previously, the radial support members 70 have a lower melting temperature than the low-density material 72, and also preferably the inner layer 50 and outer layer 54. During formation of the graft 20, heat is applied to cause melting of the support members 70 so as to fill some of the interstitial spaces in the low-density material 72 and spread out into good surface contact with the radially adjacent surfaces. Therefore, FIG. 4 illustrates the radial support members 70 having a generally rectangular longitudinal cross-section with an outer surface 90 in direct contact with the outer layer 54 (outer tube 80), and an inner surface 92 in direct contact with the adhesive layer 74. Although a certain amount of melting occurs, the extent of melting need only be enough to cause the various surfaces in contact to become laminated.

If the low-density material 72 is formed of PTFE, having a melting temperature of between about 327–341° Celsius, the radial support members 70 are made of a material with a melting temperature of less than 327° C. To avoid melting of the low-density material 72, the radial support members 70 are desirably made of the material with the melting temperature of less than 300° C. In a particular preferred embodiment, the radial support members are made of fluorinated ethylene propylene (FEP) which has a melting temperature of between about 260–300° C.

With reference again to FIG. 4, melting of the radial support members 70 creates axial blending regions 100 on either axial side of the support members. That is, the material of the support members 70 melts and flows a short distance axially into the interstitial spaces in the low-density material 72 to form the blending regions 100. In this manner, the radial support members 70 are firmly adhered to the low-density material 72, and visa versa. In addition, a radial blending region 102 is defined at the radially innermost portion of each support members 70. As will be explained below, the low-density material 72 is desirably initially tubular in form, and placed immediately around the adhesive layer 74. The radial support members 70 are then positioned around the tubular low-density material 72, so that some of the low-density material is interposed between each support member and adhesive layer 74. When heat is applied, the radial support members 70 melt and migrate radially inward to fill the interstitial spaces in the low-density material 72 between it and the adhesive layer 74, thus forming the radial blending regions 102. The radial blending regions 102 further fix the radial support members 70 relative to the low-density material 72, and visa versa.

As mentioned above, the adhesive layer 74 is made of a material that will adhere the radial support members 70 to the inner layer 50. This can be done in a number of ways, but a preferred embodiment is to provide an adhesive layer 74 that is the same material as the radial support members 70 so that the two elements will form cohesive bonds upon application of heat to the graft 20. Therefore, as seen in FIG. 4, the inner surface 90 is shown in contact with the adhesive layer 74 at a discrete surface, but the two elements are actually melted (laminated) together in the preferred embodiment to form a contiguous structure. That is, upon application of heat, the radial support members 70 are firmly melded to and along the adhesive layer 74. Significantly, because the adhesive layer 74 is tightly wrapped or otherwise securely disposed around the inner layer 50, the radial support members 70 are anchored with respect to the inner layer 50. Moreover, the adhesive layer 74, although relatively thin, also melts and will flow to a small degree radially outward into the interstitial spaces of the low-density material 72, thus further anchoring the several components both axially and circumferentially. This bonding of the radial support members 70, low-density material 72, and inner layer 50 provides the "laminated" character of the present graft 20.

In the final construction of the early access segment 40 the graft 20, the inner layer 50 and outer layer 54 substantially retain their initial shapes. At the same time, the radial support members 70 (and optionally the adhesive layer 74) are melted to a degree that permits them to flow a short distance into the interstitial spaces in the low-density material 72. The low-density material 72 does not melt, and is now firmly held in place both axially and circumferentially by the radial support members 70 and adhesive layer 74. This laminated structure is highly resistant to dissection, or separation, and remains substantially flexible because of the axially spaced nature of the radial support members 70.

FIGS. 5 and 6 illustrate the self-sealing nature of the present vascular access graft 20. The views show a portion of the wall of the early access segment 40 enlarged with only two adjacent radial support members 70 and the low-density material 72 therebetween. A needle 110 having a sharpened tip 112 and a lumen opening 114 is seen punctured through the wall of the graft in FIG. 5, and withdrawn in FIG. 6. The needle 110 is shown passing through the low-density material 72 between the adjacent radial support members 70. By virtue of the spacing and relative axial sizes of the support members 70 and low-density material 72 therebetween, a blind puncture of the vascular access graft 20 will most likely result in the needle 110 passing between adjacent support members. Because of the relatively firm (in comparison with the other components of the graft 20) radial support members 70, the exterior of the graft 20 shows a series of alternating flats 116 and ribs 118. If the graft 20 can be visualized, the medical personnel can aim the needle 110 into a region between the ribs 118 so as to pass directly through the low-density material 72. However, even if the puncture is done blind, the ribs 118 and structure of the relatively dense radial support members 70 tends to deflect the needle 110 so it passes through the low-density material 72.

The puncture 119 hole through the graft 20 is seen in FIG. 6 after the needle 110 is removed. The resiliency of the polymer materials tends to close the puncture 119 after the needle 110 is removed. In addition, the layered nature of the graft 20 further inhibits the flow of blood through the puncture 118. Most importantly, however, the blood can seep into the interstitial spaces in the low-density material 72, which promotes clotting and sealing of the puncture 119. Indeed, the puncture 119 through the low-density material 72 rapidly closes up upon removal of the needle 110 by virtue of the natural elasticity of the material in conjunction with the longitudinal compressive forces imposed thereupon. That is, because the low-density material 72 is preferably a textile-like structure, a discrete puncture hole is very difficult to discern. Instead, the needle 110 passes through the low-density material 72 without much resistance, which material then closes over the hole formed by the needle. At the same time, the low-density material 72 is firmly adhered to the adjacent radial support members 70, and to the adhesive layer 74. Therefore, although the low-density material 72 first parts around the needle 110, and then fills the puncture hole 119, it is firmly laminated in place to deter separation of the various layers of the graft 20 upon repeated punctures. In addition, the radial support members 70 resist collapse of the graft 20 from such repeated punctures.

Moreover, the presently disclosed self-sealing graft structure remains extremely flexible and capable of bending. The preferred embodiment, seen in FIGS. 1 and 2, shows the early access segment 40 in the bend 28 of the graft 20. This positioning is advantageous because the bend of the vascular access graft 20 is typically not utilized for routine needle access. The early access segment 40 can thus be used during the initial weeks of graft implantation, when the intimal fibrotic layer is forming on the remaining segments, and the straight junction portions 42a, 42b can be used when ready. In this way, the straight sections 42a, 42b having a conventional non-layered construction are used for the majority of implantation duration, and any revision procedure necessary in those areas to clear clots is simplified. Nevertheless, if a revision procedure is required in the early access segment 40, the laminated structure of inner, intermediate, and outer layers is relatively easy to incise and subsequently stitch up. Unlike some grafts of the prior art, there are not a lot of loose fibers or layers to become frayed.

In addition, the simplified structure of the early access segment 40 enables the blood pulse to be detected therethrough much easier than other, bulkier self-sealing grafts.

And after the initial tissue ingrowth period, the straight sections 42a, 42b having a conventional non-layered construction are utilized through which the pulse is easily detectable.

Figure 7A:
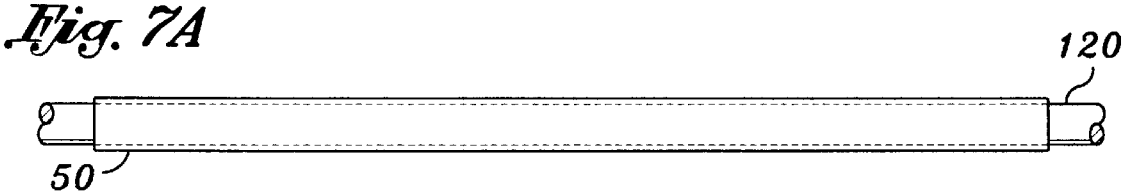
FIGS. 7A–7G are elevational views of a sequence of steps used in constructing a vascular access graft of the present invention.

A preferred method of construction of the present vascular access graft 20 will now be described which respect to FIGS. 7A–7G. FIG. 7A illustrates the inner layer 50 closely fitted around a rigid cylindrical mandrel 120. As mentioned previously, the inner layer 50 is desirably formed of a PTFE base tube 60 surrounded by a PTFE reinforcement layer 62.

Figure 7B:
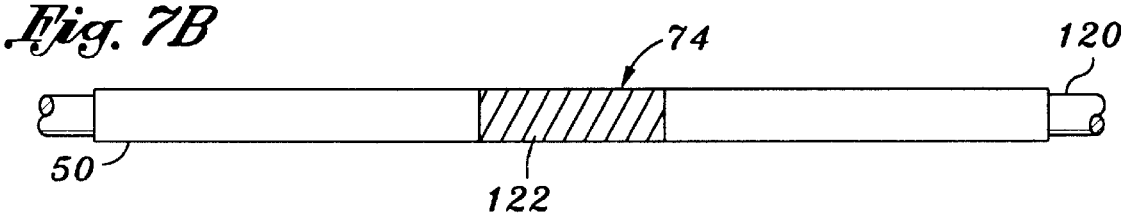

FIG. 7B shows the adhesive layer 74 added to the exterior of the inner layer 50. The adhesive layer 74 extends for an axial length substantially the same as the axial length of the early access segment 40. As mentioned above, the adhesive layer 74 is desirably a thin layer of tape made of a material that has a lower melting temperature than that of the inner layer 50. Therefore, as seen FIG. 7B, the adhesive layer 74 comprises a helically wound tape 122. The tape 122 desirably has a width of about 5 mm and is securely wrapped around the inner layer 50 in such manner as to have little or no overlap between successive turns. That is, the tape is wrapped in a single layer. In addition, the tape 122 desirably has a thickness of about 0.01 mm (0.0004 inches). As mentioned above, the adhesive layer 74 is preferably made of the same material as the radial support members 70, which in a preferred embodiment is FEP. The tape 122 is wrapped tightly around the inner layer 50 using conventional tape winding technology. Typically, the mandrel 120 rotates while a tape dispenser travels axially with respect thereto, delivering tape around the inner layer 50 at a predetermined pitch.

Figure 7C:
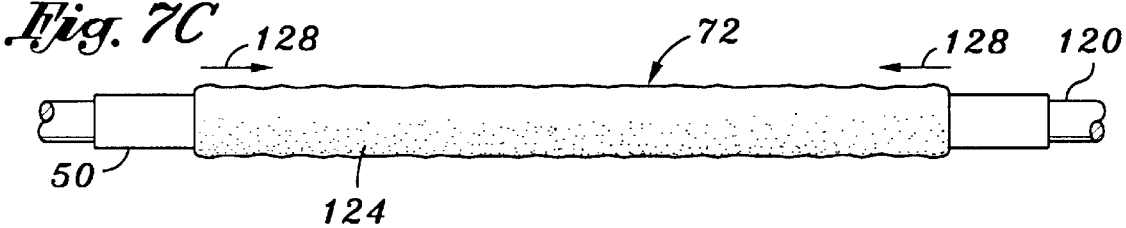

FIG. 7C shows a tube 124 of the low-density material 72 having a first length closely fitted around the inner layer 50 and adhesive layer 74. The tube 124 may be manually placed in the position shown by advancing it over a free end of the mandrel 120 (not shown). The tube 124 is longer than the ultimate length of the early access segment 40, and thus the low-density material 72 in FIG. 7C is in its uncompressed state having a first density. As mentioned above, the first density is desirably between about 0.008–0.04 g/cc. The tube 124 desirably has an initial thickness of between 0.1–2.0 mm (0.004–0.079 inches).

Figure 7D:
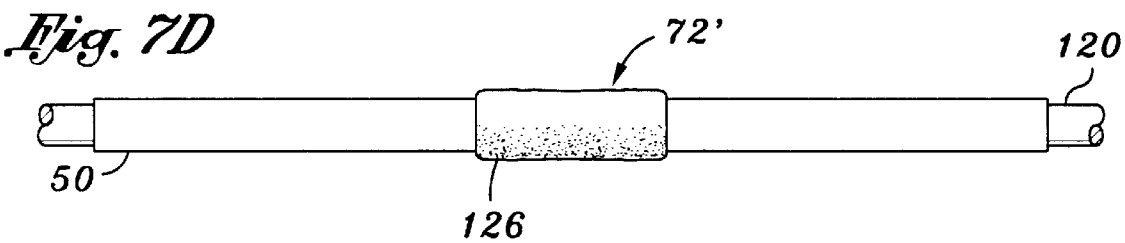

FIG. 7D illustrates a tube 126 of the low-density material 72' in its compressed state having a second length that is substantially the same as the length of the early access segment 40. To reach this state, the uncompressed tube 124 shown in FIG. 7C is compressed in the direction of the arrows 128. The axial compression of the low-density material 72 from its first length to its second length may be accomplished by manual or automated means (not shown). In a preferred embodiment, the low-density material 72 is manually longitudinally compressed. To maintain the tube 126 in its compressed state, it may be temporarily clamped or adhered to the inner layer 50. In a preferred embodiment, the tube 126 is secured by first clamping its ends and then laminating it to the adhesive layer 74 by a short heating step.

The final density of the low-density material 72 within the graft 20 depends both on the initial material density and on the degree of axial compression. The ratio between the first length shown in FIG. 7C and the second length shown in FIG. 7D provides a "packing factor" that can be used to calculate the final density. For example, if the first length shown in FIG. 7C is 12 inches, and the second length shown in FIG. 7D is 4 inches, the packing factor is 3. Desirably, the packing factor is between 2 and 4, and preferably closer to 2. By way of a specific example, if the first density is 0.04 g/cc, and the packing factor is 2, the second or final density is about 0.08 g/cc.

Figure 7E:
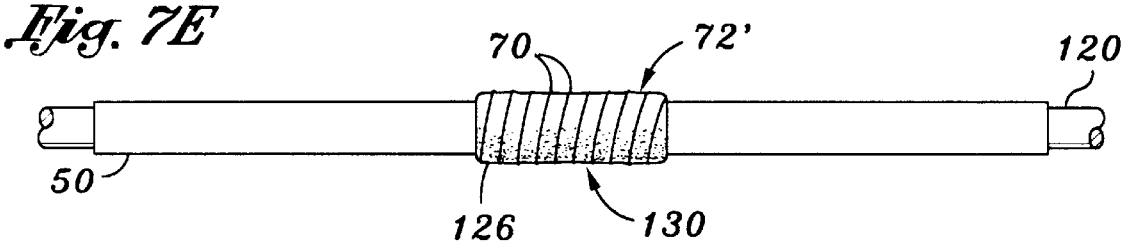

The next step in formation of the vascular access graft 20 is shown in FIG. 7E, and comprises the addition of the radial support members 70. In a preferred embodiment, the radial support members 70 comprise individual turns of a helical coil 130 wrapped tightly around the second tube 126 of compressed low-density material 72'. Each end of the coil 130 may be clamped or otherwise adhered to the second tube 126, or the inherent hoop strength of the coil 130 may be sufficient to maintain the coil in its illustrated position. Preferably, a step of heating is performed to laminate the radial support members 70 to the second tube 126 of compressed low-density material 72'. Again, the coil 130 is desirably delivered using existing wrapping technology, typically involving an axially translating spool adjacent the rotating mandrel 120. In an exemplary embodiment, the coil 130 is formed of an FEP wire having a circular cross-section with a diameter of about 0.75 mm, and is wound onto the second tube 126 with a pitch of about 5.0 mm.

Figure 7F:
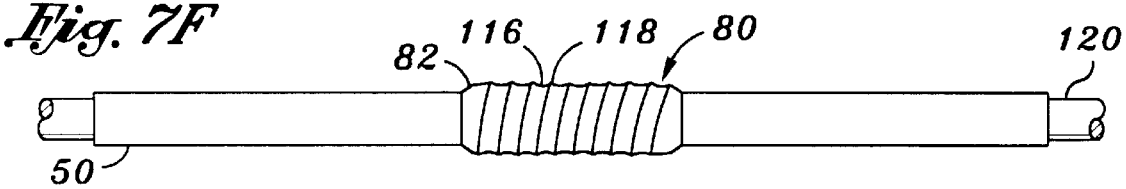

FIG. 7F shows the addition of the outer layer 54 comprising the outer tube 80. The outer tube 80 has an axial length that is slightly longer than the axial length of the second tube 126 to form the neck regions 82. The neck regions 82 are typical formed by heating of the graft 20, more fully explained below, which causes the outer tube 80 to shrink around the assembly shown in FIG. 7E. In this regard, the neck regions 82 closely conform around the inner layer 50, and around the second tube 126 and radial support members 70. Therefore, the exterior of the graft 20 shows the series of alternating flats 116 and ribs 118.

The heating step causing the melting of the radial support members 70, and shrinkage of the outer tube 80, is preferably done while the components remain on the mandrel 120. Indeed, the mandrel 120 may itself be the source of heat, or may or may not be heated and the assembly placed in an oven. Desirably, the mandrel 120 is heated to form the final graft using a variety of well-known heating techniques, such as infrared, RF, forced-air convection, or ultrasonic energy.

Figure 7G:
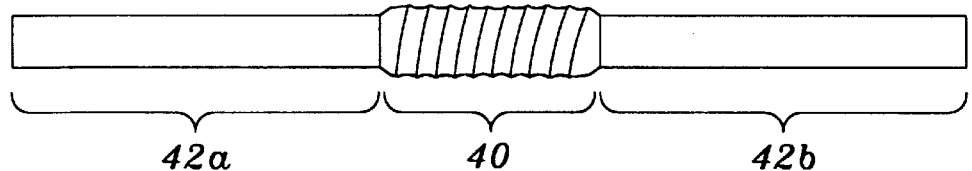

As mentioned above, the material of the radial support members 70 (and optionally the adhesive layer 74) has a melting temperature that is less than the low-density material 72, and preferably the inner layer 50 and outer layer 54 as well. Therefore, the heating step comprises heating the graft 20 to a temperature that is above the melting temperature of the radial support members 70 but below the melting temperature of the other components for a length of time sufficient to cause melting of the support members into the interstitial spaces of the low-density material 72. If the radial support members 70 are made of FEP, and the low-density material 72 is made of PTFE, the graft is preferably heated to a temperature of between 260–327° C., desirably between about 260–300° C., for a period of between about 10–20 minutes. More preferably, the graft 20 is heated to a temperature of about 280° C. for a period of about 15 minutes. Of course, the time and temperature may vary depending on the specific materials used, as long as the low-density material 72 is neither melted nor annealed into its compressed form 72'. The final form of the vascular access graft 20 is seen in FIG. 7G with the mandrel 120 removed and showing the early access segment 40 between the junction segments 42a and 42b.

Likewise, those skilled in the art understand that related, but distinct methods used with PTFE, including LASER (or the like a temperature dependent modes) fabrication steps may be readily substituted.

Alternatively, the various elements described herein can be glued together using, for example, silicone adhesive, instead of laminating them with heat. The end result is a bonded structure whether adhesives or melting is the chosen vehicle.

As mentioned above, the early access segment 40 extends along only a portion of the length of the vascular access graft 20 with the junction segments 42a and 42b or other segments (not described) constituting the remaining length. The vascular access graft 20 of the present invention desirably has a total length of between about 40–60 cm, and the early access segment 40 is between about 3–20 cm. Therefore, the early access segment 40 is between about 5–50% of the total length of the vascular access graft 20.

In use, the vascular access graft 20 is anastomosed between two vessels. The early access segment 40 enables immediate cannulation of the graft, such as for dialysis. After a suitable period of implantation, the portions of the graft other than the access segment 40 will have developed a layer of fibrotic tissue and be capable of being punctured without undue leakage. At that point, the access segment 40 is no longer punctured.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. A vascular access graft that can be punctured and will seal about the puncture hole, comprising:
    an inner tube defining an inner lumen of the graft;
    an outer tube concentrically disposed about the inner tube; and
    an intermediate tubular layer concentrically positioned between the inner and outer tubes, the intermediate tubular layer comprising, in longitudinal cross-section, alternating regions of materials of different densities, one of the materials being porous to blood, wherein the material of the inner tube is the same as the material of the outer tube.

2. The graft of claim 1, wherein the material of both the inner and outer tubes is PTFE.

3. The graft of claim 1, wherein the porous material of the intermediate layer is the same material as both the inner and outer tubes.

4. The graft of claim 3, wherein the material of both the inner and outer tubes is PTFE that is substantially non-porous to blood, and the porous material of the intermediate layer is low-density PTFE.

5. A vascular access graft that can be punctured and will seal about the puncture hole, comprising:
    an inner tube defining an inner lumen of the graft;
    an outer tube concentrically disposed about the inner tube; and
    an intermediate tubular layer concentrically positioned between the inner and outer tubes, the intermediate tubular layer comprising, in longitudinal cross-section, alternating regions of materials of different densities, one of the materials being porous to blood;
    wherein the intermediate tubular layer comprises a plurality of axially-spaced radial support members and regions of less dense material that is porous to blood axially interposed between the radial support members, and
    wherein the radial support members comprise individual turns of a helical coil.

6. The graft of claim 5, wherein the porous material of the intermediate layer is low-density PTFE and the radial support members are made of a material that has a lower melting temperature that PTFE.

7. The graft of claim 6, wherein the radial support members are made of FEP.

8. A vascular access graft that can be punctured and will seal about the puncture hole, comprising:
    an inner tube defining an inner lumen of the graft;
    an outer tube concentrically disposed about the inner tube; and
    an intermediate tubular layer concentrically positioned between the inner and outer tubes, the intermediate tubular layer comprising, in longitudinal cross-section, alternating regions of materials of different densities, one of the materials being porous to blood;
    wherein the intermediate tubular layer includes a thin adhesive layer closely surrounding the inner tube and bonded to the regions of less dense material.

9. The graft of claim 8, wherein both the radial support members and the adhesive layer are formed of materials that have lower melting temperatures than the regions of less dense material.

10. The graft of claim 9, wherein the radial support members and the adhesive layer are formed of the same material.

11. The graft of claim 10, wherein the radial support members and adhesive layer are formed of FEP, and the regions of less dense material are formed of PTFE.

12. A vascular access graft that can be punctured and will seal about the puncture hole, comprising:
    an inner tube defining an inner lumen of the graft;
    an outer tube concentrically disposed about the inner tube; and
    an intermediate tubular layer concentrically positioned between the inner and outer tubes, the intermediate tubular layer comprising, in longitudinal cross-section, alternating regions of materials of different densities, one of the materials being porous to blood,
    wherein the porous material of the intermediate layer comprises a low-density textile-like material that is longitudinally compressed from a relaxed state of the material.

13. A vascular access graft that can be punctured and will seal about the puncture hole, comprising:
    an inner tube defining an inner lumen of the graft;
    an outer tube concentrically disposed about the inner tube; and
    an intermediate tubular layer concentrically positioned between the inner and outer tubes, the intermediate tubular layer comprising, in longitudinal cross-section, alternating regions of materials of different densities, one of the materials being porous to blood,
    wherein the low-density textile-like material is made of PTFE.

14. A vascular access graft that can be punctured and will seal about the puncture hole, comprising:
    an inner tube defining an inner lumen of the graft;
    an outer tube concentrically disposed about the inner tube; and
    an intermediate tubular layer concentrically positioned between the inner and outer tubes, the intermediate tubular layer comprising, in longitudinal cross-section, alternating regions of materials of different densities, one of the materials being porous to blood, wherein the intermediate layer further includes a second material that is substantially non-porous to blood, the low-density textile-like material and second material forming, in longitudinal cross-section, the alternating regions of the vascular access graft, and wherein the vascular access graft is formed by bonding the second material to the low-density textile-like material.

15. The graft of claim 14, wherein the second material has a lower melting temperature than the low-density textile-like material, and the bonding is accomplished by laminating the second material to the low-density textile-like material.

16. The graft of claim 15, wherein the second material comprises radial support members, and the vascular access graft is formed by heating the radial support members causing them to melt and migrate into interstitial spaces formed in the low-density textile-like material.

17. A vascular access graft that can be punctured and will seal about the puncture hole, comprising:
an inner tube defining an inner lumen of the graft;
an intermediate tubular layer having a porosity and concentrically fitted around the inner tube;
a plurality of radial support members concentrically fitted around the intermediate tubular layer; and
an outer tube concentrically disposed about the intermediate tubular layer and radial support members,
wherein the plurality of radial support members define axial spaces therebetween, and the intermediate tubular layer is further axially interposed between the radial support members,
wherein the radial support members comprise individual turns of a helical coil,
wherein the intermediate tubular layer is low-density PTFE and the radial support members are made of a material that has a lower melting temperature that PTFE.

18. The graft of claim 17, wherein the radial support members are made of FEP.

19. A vascular access graft that can be punctured and will seal about the puncture hole, comprising:
an inner tube defining an inner lumen of the graft;
an intermediate tubular layer having a porosity and concentrically fitted around the inner tube;
a plurality of radial support members concentrically fitted around the intermediate tubular layer;
an outer tube concentrically disposed about the intermediate tubular layer and radial support members, and
a thin adhesive layer closely surrounding the inner tube and bonded to the intermediate tubular layer.

20. The graft of claim 19, wherein both the radial support members and the adhesive layer are formed of materials that have a lower melting temperatures than the material of the intermediate tubular layer.

21. The graft of claim 20, wherein the radial support members and the adhesive layer are formed of the same material.

22. The graft of claim 21, wherein the radial support members and adhesive layer are formed of FEP, and the intermediate tubular layer is formed of PTFE.

23. A method of manufacturing a vascular access graft, comprising:
placing an inner layer on a mandrel;
positioning a tube of low-density material over the inner layer, the tube having a first density;
compressing the tube of low-density material to a second density higher than the first density;
providing a plurality of axially spaced radial support members over the compressed tube of low-density material;
closely surrounding the assembly of the tube of low-density material and radial support members with an outer tubular layer;
bonding the aforementioned components of the vascular access graft; and
removing the mandrel.

24. The method of claim 23, wherein the step of bonding comprises heating.

25. The method of claim 24, where the radial support members are made of the material that has a lower melting temperature than the melting temperature of low-density material, and the step of heating comprises heating the graft to a temperature between the respective melting temperatures of the radial support members and the low-density material.

26. The method of claim 25, wherein the radial support members are made of FEP and the low-density material is made of PTFE.

27. A product, produced by the method of claim 26.
28. A product, produced by the method of claim 25.
29. A product, produced by the method of claim 24.
30. The method of claim 23, wherein the step of compressing comprises:
longitudinally compressing the tube of low-density material to a second length shorter than the first length.
31. A product, produced by the method of claim 30.
32. A product, produced by the method of claim 23.

* * * * *

UNITED STATES PATENT AND TRADEMARK OFFICE
CERTIFICATE OF CORRECTION

PATENT NO.    : 6,319,279 B1
DATED         : November 20, 2001
INVENTOR(S)   : Don Shannon, Chris Kuo and Benny Tu It is certified that error appears in the above-identified patent and that said Letters Patent is hereby corrected as shown below:

<u>Title page,</u>
Item [73] Assignee: Edwards Lifesciences Corp., Irvine, CA (US)

<u>Column 5,</u>
Line 53, replaced "recognine" with -- recognize --.

<u>Column 10,</u>
Line 66, replaced "a temperature" with -- atemperature --.

Signed and Sealed this

Fourth Day of June, 2002

*Attest:*

*Attesting Officer*

JAMES E. ROGAN
*Director of the United States Patent and Trademark Office*